(12) United States Patent
Owens

(10) Patent No.: US 8,552,044 B1
(45) Date of Patent: Oct. 8, 2013

(54) COATINGS FOR DISEASE CONTROL

(75) Inventor: Jeffery R. Owens, Panama City, FL (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 819 days.

(21) Appl. No.: 12/543,576

(22) Filed: Aug. 19, 2009

Related U.S. Application Data

(60) Provisional application No. 61/090,337, filed on Aug. 20, 2008.

(51) Int. Cl.
*A61K 31/4188* (2006.01)
*C07D 487/04* (2006.01)

(52) U.S. Cl.
USPC .................................... 514/393; 548/303.4

(58) Field of Classification Search
None
See application file for complete search history.

(56) References Cited

U.S. PATENT DOCUMENTS 6,271,326 B1 * 8/2001 Nishikawa et al. ........... 526/242
6,436,419 B1   8/2002 Sun et al.
6,969,769 B2  11/2005 Worley et al.

FOREIGN PATENT DOCUMENTS

WO   WO2007031775 A2 *  3/2007

OTHER PUBLICATIONS

S.D. Worley et al., "Biocidal Polymers", TRIP, Nov. 1996, pp. 364-370, vol. 4, No. 11.
Y. Chen et al., "Biocidal! Polystyrene Beads. IV. Functionalized Methylated Polystyrene", Journal of Applied Polymer Science, 2004 pp. 368-372, vol. 92, Wiley Periodicals, Inc.
Y. Sun et al., "Novel Refreshable N-Halamine Polymeric Biocides: N-Chlorination of Aromatic Polyamides", Ind. Eng. Chem. Res. 2004, pp. 5015-5020, vol. 43.
Y. Sun et al., "Novel Refreshable N-Halamine Polymeric Biocides: Grafting Hydantoin-Containing Monomers onto High Performance Fibers by a Continuous Process", Journal of Applied Polymer Science, 2003, pp. 1032-1039, vol. 88, Wiley Periodicals, Inc.
S.D. Worley et al., "A Novel N-Halamine Monomer for Preparing Biocidal Polyurethane Coatings", Technical Report AFRL-ML-TY-TP-2002-4629. 2002.
M. B. Harney et al., "Surface Self-Concentrating Amphiphilic Quaternary Ammonium Biocides as Coating Additives", ACS Applied Materials & Interfaces, American Chemical Society. Accepted for publication Sep. 16, 2008, Nov. 24, 2008.

* cited by examiner

*Primary Examiner* — Michael Barker
(74) *Attorney, Agent, or Firm* — AFMCLO/JAZ; Fredric Sinder

(57) ABSTRACT

The present invention relates to coatings for disease control. More particularly, the present invention relates to coatings that are effective against toxins, precursors to these coatings and methods of forming the coatings.

3 Claims, No Drawings

US 8,552,044 B1

COATINGS FOR DISEASE CONTROL

PRIORITY

This application claims priority from the USPTO provisional patent application entitled "Coatings for Disease Control" filed on Aug. 20, 2008, Ser. No. 61/090,337 which is hereby incorporated herein by reference.

RIGHTS OF THE GOVERNMENT

The invention described herein may be manufactured and used by or for the Government of the United States for all governmental purposes without the payment of any royalty.

BACKGROUND OF THE INVENTION

The present invention relates to coatings for disease control. More particularly, the present invention relates to coatings that are effective against toxins, precursors to these coatings and methods of forming the coatings.

Toxins are biologically-derived molecules that cause disease. They include prions, proteins, polysaccharides, enzymes, nucleic acids and histones. They are, by definition, non-living in contrast to other disease vectors such as pathogens.

In the past, much less research has focused on methods of deactivating toxins compared to killing pathogens because it has been assumed that the most convenient way to render a toxin ineffective is simply to purge the toxin from a system. However, recently it has been found that toxins can be deactivated by materials so that they no longer exhibit their toxic effects. This discovery has partly resulted from an increased interest in toxins caused by events: for example, various protein-based toxins such as ricin and Botulinal toxin have been become more widely available for use as biological weapons.

The greater emphasis in the past on the killing of pathogens such as bacteria, fungi, yeasts and also viruses has caused much effort being made to develop substances that kill these pathogens. This research has resulted in the design of many substances collectively called 'biocides' that are effective against pathogens. However, little effort has yet been made to develop substances that deactivate toxins. What research that has been done to date has shown that different mechanisms operate in killing pathogens and in deactivating toxins. Therefore, materials that kill pathogens are often not effective against toxins and, as a result, new materials need to be developed that are effective against toxins.

SUMMARY OF THE INVENTION

The present invention aims to address at least some of the problems of the prior art. Accordingly, the present invention provides in a first aspect a method for forming a coating on a substrate for deactivation of toxins, the method comprising: providing a compound containing a glycoluril functional group and a siloxane monolayer precursor group, applying the compound to the surface, and exposing the surface to microwave electromagnetic radiation.

In a second aspect, the present invention provides a method for forming a coating for deactivation of toxins on a substrate, the method comprising: providing a compound containing a functional group containing at least two hydrogen atoms attached to one or more nitrogen atoms and a compound containing a cross-linking siloxane precursor group and applying the compounds to the surface.

In a third aspect, the present invention provides substrate having a compound containing a glycoluril functional group attached to, and/or organized into an array on a surface by being treated by the method of the first or second aspects.

In a fourth aspect, the present invention provides a compound having the structure:

(6)

$$\begin{array}{c} R_1 \quad R_5 \quad R_2 \\ \diagdown \quad | \quad \diagup \\ N \quad \quad N \\ HN = \quad \quad = NH \\ N \quad \quad N \\ \diagup \quad | \quad \diagdown \\ R_4 \quad R_6 \quad R_3 \end{array}$$

wherein: $R_1$, $R_2$, $R_3$ and $R_4$, $R_5$ and $R_6$ are independently selected from hydrogen, the halogens (in one embodiment chlorine or bromine), alkyl, heteroalkyl, a group containing a siloxane monolayer precursor, OH, O-alkyl, O-heteroalkyl, $NH_2$, NH(alkyl), NH(heteroalkyl), N(alkyl)(alkyl), N(alkyl)(heteroalkyl) and N(heteroalkyl)(heteroalkyl), and at least one of $R_1$, $R_2$, $R_3$, $R_4$, $R_5$ and $R_6$ is a group containing a siloxane monolayer precursor.

In a fifth aspect, the present invention provides a compound having the structure:

$$\begin{array}{c} R_1 \quad R_5 \quad R_2 \\ \diagdown \quad | \quad \diagup \\ N \quad \quad N \\ X_1 = \quad \quad = X_2 \\ N \quad \quad N \\ \diagup \quad | \quad \diagdown \\ R_4 \quad R_6 \quad R_3 \end{array}$$

wherein: $X_1$ and $X_2$ are independently-selected heteroatoms, optionally having one or more pendant independently-selected alkyl and/or independently-selected heteroalkyl groups and/or hydrogen, $R_1$, $R_2$, $R_3$ and $R_4$, $R_5$ and $R_6$ are independently selected from hydrogen, the halogens (in one embodiment chlorine or bromine), alkyl, heteroalkyl, OH, O-alkyl, O-heteroalkyl, $NH_2$, NH(alkyl), NH(heteroalkyl), N(alkyl)(alkyl), N(alkyl)(heteroalkyl) and N(heteroalkyl)(heteroalkyl), and at least one of $R_1$, $R_2$, $R_3$, $R_4$, $R_5$ and $R_6$ is a group containing a vinyl group, an imide, an acrylate, an alkene, an epoxide or an alkyl halide.

In a sixth aspect, the present invention provides a method for forming a coating for deactivation of toxins on a substrate, the method comprising: providing the compound of the fifth aspect, applying the compound to the surface, and exposing the surface to microwave electromagnetic radiation.

In a seventh aspect, the present invention provides a substrate having a compound containing a glycoluril functional group attached to, and/or organized into an array on the surface by the method as defined in the sixth aspect.

The present invention also provides the use of a coating formed from a compound containing a glycoluril functional group and a siloxane monolayer precursor group in the deactivation of toxins. The present invention also provides the use of a coating formed by the method as defined in the second aspect in the deactivation of toxins.

Finally, the present invention provides a method for forming a coating on a substrate, the method comprising: providing a compound containing a glycoluril functional group and a compound containing a cross-linking siloxane precursor, and applying the compound to the surface.

DETAILED DESCRIPTION

The inventor of the present invention has found one particular class of molecules that is effective against toxins when attached to a surface in a particular way. This molecule includes a glycoluril functional group. The molecule further includes a siloxane monolayer precursor group so that the glycoluril functional group is attached to a surface and/or organized into an array at the surface by reaction of the surface with the siloxane monolayer precursor.

Conventionally, this molecule would be attached to the surface by heat treatment as in U.S. Pat. No. 6,969,769. However, the inventor has found that this method of attachment of the molecule to the surface does not result in a surface that is effective against toxins. Instead, the inventor has found that it is necessary to attach this molecule to a surface under the irradiation of microwaves in order for it to form a surface that is effective against toxins.

Accordingly, in a first aspect, the present invention provides a method for attaching compounds containing both a glycoluril functional group and a siloxane monolayer precursor group to a surface by exposing the surface to the compound while being treated with microwaves.

As used herein, the term "microwaves" refers to electromagnetic radiation having a frequency from 0.3 to 30 GHz. Alternatively, the microwaves may have a frequency of 0.3 to 10 GHz, or from 1 to 3 GHz. The microwaves may be produced using a power rating of 650 Watts or less, for example 65 to 650 Watts, or 135 to 400 Watts.

As used herein, the term "siloxane monolayer precursor" refers to a group that is able to form a siloxane monolayer at the surface of a substrate. Siloxane monolayer precursors are well-known to the person skilled in the art.

Typically, the surfaces for use in the present invention contain a number of nucleophilic sites on their surface, so reaction of the siloxane monolayer precursor with a surface typically involves the nucleophilic displacement of a leaving group attached to the silicon by one of the nucleophilic sites on the surface of the substrate. At the same time, the siloxane monolayer precursor may also react with other siloxane monolayer precursor molecules in a cross-linking reaction to from the Si—O—Si (siloxane) functional group to form an organized array of molecules. In addition, the term "siloxane monolayer precursor" includes within its scope pre-formed siloxane groups, such as siloxane polymers. This overall process is known as the self-assembly of a monolayer at the surface.

It should be noted that the term "siloxane monolayer precursor" does not require the formation of a complete monolayer over the surface of a substrate. In fact, the formation of a complete surface-covering monolayer involves the careful control of reaction conditions and selection of precursors. Rather, the term simply requires that some of the siloxane monolayer precursor groups contain groups such as leaving groups that can be displaced by nucleophiles that can react with the surface of a substrate. If the siloxane monolayer precursor does not already contain siloxane bonds, the precursor may also be able to self-react with other siloxane monolayer precursor molecules (self-reaction usually occurs after the displacement of a leaving group with, for example, water, followed by reaction of the newly formed Si—OH with a second siloxane monolayer precursor). In addition, the term does not exclude precursor molecules that form multi-layers rather than single monolayers.

As previously noted, examples of siloxane monolayer precursors are well-known to the person skilled in the art. Siloxane monolayer precursors include compounds containing silicon-$X_3$ functional groups, wherein $X_3$ is a leaving group. $X_3$ may be, for example, a halogen, O-alkyl, O-heteroalkyl, OH, $NH_2$, NH-alkyl, NH-heteroalkyl, N(alkyl)(alkyl), N(alkyl)(heteroalkyl) or N(heteroalkyl)(heteroalkyl). Siloxane monolayer precursors also include pre-formed siloxane polymers themselves.

For example, the siloxane monolayer precursor may be selected from a siloxane compound, a silanol compound, a silyl ether compound, a silanolate compound, a halosilane compound, a silatrane compound and a silazane compound.

As used herein, the term "glycoluril functional group" refers to a compound containing the following chemical structure:

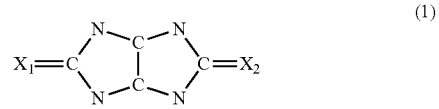

(1)

being treated by the method of the first or second aspects.

In this structure, $X_1$ and $X_2$ are independently-selected optionally-substituted heteroatoms (i.e., atoms other than carbon). The heteroatoms may be substituted with one or more independently-selected alkyl and/or heteroalkyl groups (as defined below) and/or hydrogen as appropriate. For example, $X_1$ and/or $X_2$ may be oxygen, nitrogen or sulphur. If either or both of $X_1$ or $X_2$ is nitrogen or another atom having a valency of three or more, $X_1$ and/or $X_2$ is substituted with further substituents. For example, $X_1$ and/or $X_2$ may have the chemical formula $NR_7$. In a preferred embodiment, $R_7$ (or any other substituent(s)) is hydrogen. Alternatively, $R_7$ (or any other substituent(s) on any heteroatom) may be OH, O-alkyl, O-heteroalkyl, alkyl or heteroalkyl. It is to be noted that the carbon-carbon bond shown in the above structure may be a single bond or a double bond.

As used herein, the term "alkyl" refers to a group containing carbon and hydrogen. The alkyl group may itself be unsubstituted (i.e., contain only carbon and hydrogen) or, alternatively, it may be substituted with heteroatom-containing substituents. The alkyl group may straight-chained or it may be branched or it may cyclic, or combinations thereof. The alkyl group may be saturated, partially or completely unsaturated or aromatic. For example, the alkyl group may comprise one or more alkene and/or alkyne functional groups.

The alkyl group contains any number of carbon atoms. In one embodiment, the alkyl group contains 1 to 25 carbon atoms. In one embodiment, the alkyl group contains 1 to 10 carbon atoms, for example 1 to 6 carbon atoms.

Examples of possible saturated unsubstituted alkyl groups having 1 to 6 carbon atoms include methyl, ethyl, n-propyl, sec-propyl, cyclopropyl, n-butyl, sec-butyl, tert-butyl, cyclobutyl, pentyl (branched or unbranched) and hexyl (branched or unbranched). Examples of possible saturated unsubstituted alkyl groups having 1 to 6 carbon atoms further include cyclic carbon compounds, for example a cyclopropyl group, a cylcobutyl group, a cyclopentyl group and a cyclohexyl group.

If the alkyl group is substituted, it may be partially substituted or completely substituted with one or more independently selected heteroatoms or groups of heteroatoms. Examples of heteroatom substituents include the halogens, including fluorine, chlorine, bromine or iodine, —OH, =O, —NH$_2$, =NH, —NHOH, =NOH, —OPO(OH)$_2$, —SH, =S or —SO$_2$OH. If the alkyl group is substituted with =O, the alkyl group may comprise an aldehyde, a ketone, a carboxylic acid or an amide. (It is to be noted that heteroatoms themselves substituted with alkyl groups are included within the scope of the present invention under the term "heteroalkyl").

The alkyl group may be or may comprise an aryl group. The term "aryl" group refers to a group comprising one or more aromatic cycles. The cycle is made from carbon atoms. An example of an aryl substituent is a phenyl group.

As used herein, the term "heteroalkyl" group refers to a first alkyl group substituted with one or more independently-selected heteroatoms or groups of heteroatoms, which itself is substituted with one or more independently-selected groups containing one or more carbon atoms. As an illustrative example, an ester group is a heteroalkyl group because a first alkyl group is substituted with oxygen, which itself is substituted with a second alkyl group. As such, a heteroalkyl can be represented by the generic formula R$_8$—Y—R$_9$, where R$_8$ is an alkyl group, Y is one or more heteroatoms and R$_9$ contains one or more carbon atoms and optionally one or more heteroatoms and connects to Y through a carbon atom (e.g. an alkyl group). It is also to be noted that R$_8$ and R$_9$ may be joined to one another so as to form a cyclic group containing one or more heteroatoms.

The heteroalkyl group may itself be unsubstituted (i.e. contain only carbon, hydrogen and the heteroatom or groups of heteroatom contained in the backbone of the heteroalkyl group) or, alternatively, it may be substituted with heteroatom-containing substituents. The heteroalkyl group may straight-chained or it may be branched or it may cyclic, or combinations thereof. The heteroalkyl group may be saturated, partially or completely unsaturated or aromatic.

The heteroalkyl group contains any number of carbon atoms. In one embodiment, the heteroalkyl group contains a total of 1 to 25 carbon atoms. In one embodiment, the heteroalkyl group contains a total of 1 to 10 carbon atoms, for example 1 to 6 carbon atoms.

Examples of heteroatoms in heteroalkyl groups include: nitrogen, oxygen, phosphorus and sulfur. In one embodiment, Y as defined above is oxygen. In this case, Y may for example be part of an ether group (—O—R$_9$) or an ester (—O—CO—R$_9$). In another embodiment, Y is a nitrogen atom. In this case, Y may for example be part of one of the following groups: —NR$_9$H, —NR$_9$R$_{10}$, —NR$_9$R$_{10}$R$_{11}$ (with an appropriate counter-ion), —NH—CO—R$_9$ and —NR$_{10}$—CO—R$_9$. R$_{10}$ itself contains one or more carbon atoms and optionally one or more heteroatoms and connects to Y through a carbon atom (e.g. an alkyl group).

The heteroalkyl group may be or may comprise cyclic groups containing a heteroatom. For oxygen and nitrogen heteroatoms, examples of such groups include a lactone, lactam or lactim. Further examples of heteroalkyl groups include azetidines, oxetane, thietane, dithietane, dihydrofuran, tetrahydrofuran, dihydrothiophene, tetrahydrothiophene, piperidine, pyrroline, pyrrolidine, tetrahydropyran, dihydropyran, thiane, piperazine, oxazine, dithiane, dioxane and morpholine.

The heteroalkyl group may be unsubstituted or substituted with one or more hetero-atoms or group of hetero-atoms. Alternatively or in addition, the heteroalkyl group may be substituted with one or more heteroatoms or groups of heteroatoms that are themselves substituted with one or more independently selected alkyl groups. Further substitution of these one or more alkyl groups is also contemplated, so that the number of groups of heteroatoms or groups of heteroatoms which are substituted with alkyl groups and the number of alkyl groups substituted with heteroatoms or groups of heteroatoms which are themselves substituted with one or more alkyl groups are not limited. If more than one hetero-substituent is present, the substituents are independently selected from one another unless they form a part of a particular functional group (e.g., an amide group). One or more of the substituents may be a halogen atom, including fluorine, chlorine, bromine or iodine, —OH, =O, —NH$_2$, =NH, —NHOH, =NOH, —OPO(OH)$_2$, —SH, =S or —SO$_2$OH. If the heteroalkyl group is substituted with =O, the heteroalkyl group may comprise an aldehyde, a ketone, a carboxylic acid or an amide.

The heteroalkyl group may be or may comprise a heteroaryl group. The term "heteroaryl" refers to group comprising one or more aromatic cycles. The cycle is made from carbon atoms and heteroatoms. The one or more heteroatoms are independently-selected from, for example, nitrogen, oxygen, phosphorus and sulphur. Examples of heteroaryl groups include pyrrole, furan, thiophene, pyridine, melamine, pyran, thiine, diazine and thiazine.

In one embodiment, the first aspect of the present invention uses a glycoluril compound having the following structure:

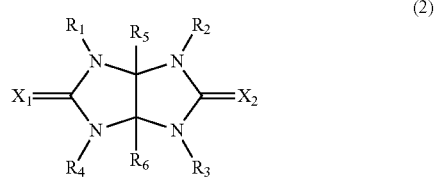

(2)

In formula (2), X$_1$ and X$_2$ are independently-selected optionally-substituted heteroatoms (i.e. atoms other than carbon). For example, X$_1$ and/or X$_2$ may be oxygen, nitrogen or sulphur. If either X$_1$ or X$_2$ is nitrogen, the nitrogen is substituted with a third substituent, i.e. X$_1$ and/or X$_2$ have the chemical formula NR$_7$. In a preferred embodiment, this third substituent (R$_7$) is hydrogen. Alternatively, R$_7$ (or any optional substituent) may for example be OH, O-alkyl, O-heteroalkyl, alkyl or heteroalkyl.

In formula (2), R$_1$, R$_2$, R$_3$ and R$_4$ are independently selected from hydrogen, the halogens (in one embodiment chlorine or bromine), alkyl, heteroalkyl and a siloxane monolayer precursor-containing group. In one embodiment, at least one of R$_1$, R$_2$, R$_3$ and R$_4$ is hydrogen, a halogen (in one embodiment chlorine and/or bromine) or a protecting group for hydrogen (protecting groups are well-known in the art: see, for example, the book "*Protective Groups in Organic Synthesis*" by Greene et al.). R$_5$ and R$_6$ are independently selected from hydrogen, the halogens (in one embodiment chlorine or bromine), alkyl, heteroalkyl and a siloxane monolayer precursor-containing group, OH, O-alkyl, O-heteroalkyl, NH$_2$, NH(alkyl), NH(heteroalkyl), N(alkyl)(alkyl), N(alkyl)(heteroalkyl) and N(heteroalkyl)(heteroalkyl). At least one of R$_1$, R$_2$, R$_3$, R$_4$, R$_5$ and R$_6$ is a siloxane monolayer precursor-containing group.

The at least one siloxane monolayer precursor-containing group may have the following chemical structure:

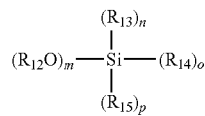
(3)

or a polymer have repeating units of formula (4), which may be terminated by hydrogen, hydroxyl, an alkyl or an amine group at one or both ends of the polymer chain:

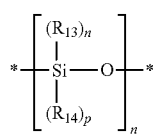
(4)

wherein: $R_{12}$ is hydrogen or an alkyl group or a heteroalkyl group, in one embodiment a $C_1$ to $C_6$ alkyl, in one embodiment, a $C_1$ or $C_2$ alkyl, such as methyl or ethyl, and m is 1 to 4, in one embodiment 3;

$R_{13}$, $R_{14}$ and $R_{15}$ are each independently selected from alkyl, aminoalkyl, heteroalkyl and aminoheteroalkyl, in formula (3), n, o and p are each 0 to 3, providing that m+n+o+p=4, (m+n+o+p can also equal up to 6), in formula (4), n and p are each 0, 1 or 2, providing that n+p=2, and at least one of $R_{13}$, $R_{14}$ and $R_{15}$ contains a glycoluril functional group.

Other leaving groups may replace $OR_{12}$ in formula (3) above, for example one or more halogens (e.g. Cl). Leaving groups may also replace $R_{13}$ or $R_{14}$ in formula (4) above.

Examples of alkyl and heteroalkyl groups for use in the present invention include groups containing glycidoxy groups, amino groups, acrylates and groups containing alkenes.

The polymer defined above in one embodiment includes electron donor groups on at least some of its monomers. These electron donor groups may be substituents on $R_{13}$ and/or $R_{14}$ in formula (4) above or on $R_{13}$ and/or $R_{14}$ and/or $R_{15}$ in formula (3) above. Electron donor groups include, but are not limited to, hydroxyl, amine, sulfhydryl and carboxyl. X, the number of repeating units in the polymer, may be any appropriate number. X may be 2 to 10000, in one embodiment 2 to 1000.

In one embodiment, $R_{12}$, $R_{13}$, $R_{14}$ and/or $R_{15}$ are substituted with one or more halogens. In one embodiment, the halogens are located at the distal end of the group(s) from the silicon. In one embodiment, the halogen is chlorine.

In one embodiment, the siloxane monolayer precursor-containing compound is a compound of formula (3), wherein m is 3, n is 1 and o and p are both 0, $R_{12}$ is hydrogen, methyl or ethyl.

In one embodiment, at least one of $R_{13}$, $R_{14}$ and/or $R_{15}$ is of the formula (5):

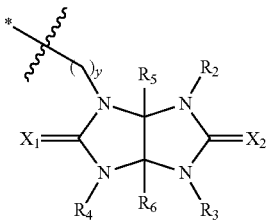
(5)

wherein y is 1 to 5, in one embodiment 3.

In one embodiment $R_5$ and/or $R_6$ is/are a UV-stabilizing group.

In order to deposit the siloxane monolayer precursor-containing compound on a surface, a solution or suspension of the silicon-containing compounds may be contacted with the surface. The solution and/or suspension in one embodiment comprises a polar solvent, in one embodiment acetone and/or alcohol. The alcohol in one embodiment comprises methanol and/or ethanol. Alternatively, the siloxane monolayer precursor-containing compound may be solvent-free, i.e. not in the form of a solution or suspension, for example in the form of a liquid or gas (but preferably not a plasma).

The surface of the substrate is in one embodiment a material having nucleophilic sites on its surface. The nucleophilic sites may comprise one or more nucleophilic groups containing one or more of O, S and N. For example, the nucleophilic groups may be oxygen-containing, nitrogen-containing and/or sulfur-containing, for example selected from OH, SH and $NH_2$. The substrate may comprise a fabric material. It has been found that the nucleophilic groups bind to the silicon atoms of the siloxane monolayer precursor-containing compounds on contact and with exposure to microwaves. This reaction normally occurs within seconds, as opposed to hours for conventional methods, such as merely heating.

In practice, in order to reduce the possible degradation of delicate siloxane monolayer precursor-containing compounds and/or delicate substrates, one or more of the following may be used: irradiation at a reduced power level, for example microwaves produced at a power rating of 400 Watts or less, in one embodiment 135 Watts or less, or subjecting the substrate and siloxane monolayer precursor-containing compounds to microwave irradiation and relaxation (i.e. no microwave irradiation) in alternating intervals: for example a period of irradiation of 5 to 30 seconds, alternatively 10 to 20 seconds, or about 15 seconds, followed by a period of relaxation of about 2 to 30 seconds, alternatively 5 to 15 seconds, or about 10 seconds, and optionally repeating this process as often as required. It has been found that, for many compounds containing an Si—O moiety, this is more sensitive to microwave radiation than other 'delicate' functionalities and therefore cleavage of the Si—O bond may be achieved without degradation of the other functionalities.

The microwaves can be directed at particular portions of the substrate and therefore allow for regioselective attachment and/or arrangement of the silicon-substituted compounds and for reactions that can be initiated that would not be possible using traditional methods.

The substrate may comprise a natural material. The material may be a cloth material. The material may comprise one or more materials selected from cotton, wool and leather. The material may be woven or non-woven. The material may comprise fibers of natural and/or synthetic material. The synthetic material may comprise a woven or nonwoven fabric material to include, but limited to, fabrics wherein the material comprises one or more of cotton, polyester, nylon, wool, leather, rayon, polyethylene, polyvinylchloride, polyvinylalcohol, polyvinylamine and polyurea.

The substrate may be in the form of particles. The particles may have a diameter of 10 nm to 1 mm, in one embodiment 100 to 1000 nm.

The substrate may comprise a metal oxide. The metal oxide may be selected from one or more of aluminum oxide, titanium dioxide, magnesium oxide, calcium oxide, silicon dioxide and zinc oxide.

The substrate may comprise a natural mineral. The substrate may comprise one or more materials selected from kaolinite, barasym, silica, montmorillonite, vermiculite, bohemite and quartz.

The substrate may be porous. The substrate may comprise a molecular sieve. The substrate may comprise a zeolite.

The substrate may comprise a polymer. The polymer may be in the form of a porous matrix. The substrate may comprise a plastic material. The substrate may comprise polyurethane and/or nylon, plyester, nylon, rayon, polyethylene, polyvinylchloride, polyvinylalcohol, polyvinylamine and polyurea.

The substrate may comprise a carbohydrate.

An alcohol may be present during deposition of the coating. In particular, the substrate may comprise an alcohol. The substrate may have an alcohol on its surface. The alcohol may comprise a diol, which may be a vicinal diol, or a triol. The alcohol may be selected from one or more of an alkyl diol, in one embodiment a $C_2$ to $C_{25}$ alkyl diol, an alkyl trio, in one embodiment a $C_3$ to $C_{25}$ alkyl triol and a phenyl diol, alternatively a vicinal phenyl diol. Each hydroxyl group in the triol is in one embodiment vicinal to one of the other hydroxyl groups. The alcohol may be selected from catechol, ethylene glycol or glycerol.

The substrate may comprise a silicon dioxide based material, such as glass, silicon dioxide, sand and silica.

In order to give the glycoluril functional group of the present invention its disease-prevention properties, the glycoluril group should have at least one of its nitrogen substituted with a halogen, for example chlorine or bromine (i.e. at least one or $R_1$, $R_2$, $R_3$ and $R_4$ should be a halogen). The halogen may be introduced at any stage. For example, it may be introduced prior to the deposition of the coating on the substrate. Alternatively, it may be introduced after the deposition of the coating on the substrate. For example, the glycoluril group may be halogenated with an oxidative halogen compound, such as a hypochlorite, for example aqueous sodium hypochlorite.

Following treatment of the substrate with the halogenating agent, the substrate may be dried. The substrate may be dried by exposing it to a temperature of about 20° C. or more, alternatively about 30° C. or more, or about 35° C. for a period including, but not limited to, 1 hour or more, in one embodiment 4 hours or more.

In a second aspect, the present invention provides a different method for attaching compounds containing disease-preventing functional groups to a surface. This method involves providing a compound containing at least two hydrogen atoms attached to one or more nitrogen atoms, and a separate compound containing a cross-linking siloxane precursor group. (In other words, the compound contains either $NH_2$ or $NH_3$, or two or more nitrogens of the formula $NH_x$, where x is 1 to 3 and where x is independently selected for each amine functional group. Other groups are of course attached to the $NH_x$ as so defined). The compounds are applied to the surface the compounds to the surface. In one embodiment, the surface is then exposed to microwave electromagnetic radiation (either at the same time or shortly afterwards).

As used herein, the term "compound containing a siloxane precursor cross-linking group" refers to a compound that contains one or more silicon atoms that are in total capable of reaction with at least two nucleophiles. In use, the compound is capable of reacting with the surface (whose preferable characteristics are the same as the first aspect), with the glycoluril compound itself and optionally with itself (to form a siloxane polymer).

In total, the siloxane precursor cross-linking compound may be able to undergo at least two reactions in which nucleophiles displace a leaving group at one or more silicon atom. In other words, in this embodiment the compound may contain a total of at least two leaving groups. These may append either the same silicon atom or, if the compound contains more than one silicon atoms, these may append different silicon atoms. With at least two leaving groups, the compound is able to both react with a surface and also with a glycoluril-containing compound. As such, its function in this embodiment is to cross-link the surface to the glycoluril-containing compound.

The leaving groups appended to the silicon atom(s) in this second aspect are the same as in the first aspect. In particular, the leaving groups may be silicon-$X_3$ functional groups, wherein $X_3$ is hydrogen, a halogen, O-alkyl, O-heteroalkyl, OH, $NH_2$, NH-alkyl, NH-heteroalkyl, N(alkyl)(alkyl), N(alkyl)(heteroalkyl) or N(heteroalkyl)(heteroalkyl). Alternatively or additionally, siloxane polymers themselves may be suitable.

In one embodiment, the siloxane precursor cross-linking compound has a total of at least three leaving groups appending one or more silicon atom(s). This is so that they may undergo three separate reactions, namely reaction with a surface, reaction with the glycoluril-containing compound and self-reaction to form a organized array. For example, the siloxane precursor cross-linking compound may comprise at least four leaving groups appending silicon atoms.

Examples of suitable siloxane precursor cross-linking compounds include compounds having the chemical structure:

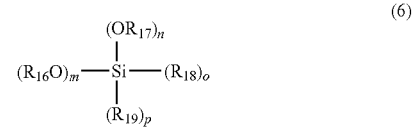

(6)

wherein in formula (6) m and n are each 0 to 4, o and p are each 0 to 2, providing that m+n+o+p=4, and m+n is at least 2, in one embodiment 3, for example 4, (m+n+o+p can also equal up to 6), or a polymer have repeating units of the following formula, which may be terminated by hydrogen, hydroxyl, an alkyl or an amine group at one or both ends of the polymer chain:

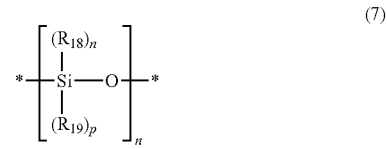

(7)

wherein:

$R_{16}$ and $R_{17}$ are independently selected from hydrogen, an alkyl group or a heteroalkyl group, in one embodiment a $C_1$ to $C_6$ alkyl, in one embodiment, a $C_1$ or $C_2$ alkyl, such as methyl or ethyl; $R_{18}$ and $R_{19}$ are each independently selected from alkyl, aminoalkyl, heteroalkyl and aminoheteroalkyl, in formula (7), n and p are each 0, 1 or 2, providing that n+p=2.

Other leaving groups may replace $OR_{16}$ or $OR_{17}$ in formula (6) above, for example one or more halogens (e.g. Cl). Leaving groups may also replace $R_{18}$ or $R_{19}$ in formula (7) above.

The polymer defined above in one embodiment includes electron donor groups on at least some of its monomers. These electron donor groups may be substituents on $R_{18}$ and/or $R_{19}$ in formulas (6) and (7) above. Electron donor groups include, but are not limited to, hydroxyl, amine, sulfhydryl and carboxyl. X, the number of repeating units in the polymer, may be any appropriate number. X may be 2 to 10,000, in one embodiment 2 to 1,000.

In one embodiment, $R_{18}$ and/or $R_{19}$ are substituted with one or more halogens. In one embodiment, the halogens are located at the distal end of the group(s) from the silicon. In one embodiment, the halogen is chlorine.

In one embodiment, the siloxane precursor cross-linking compound is a compound having the following structure:

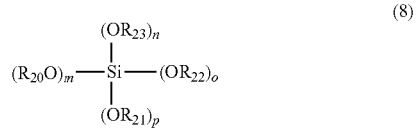

(8)

where $R_{20}$, $R_{21}$, $R_{22}$ and $R_{23}$ are independently selected from hydrogen, an alkyl group or a heteroalkyl group, in one embodiment a $C_1$ to $C_6$ alkyl, in one embodiment, a $C_1$ or $C_2$ alkyl, such as methyl or ethyl. In one embodiment, $R_{16}$, $R_{17}$, $R_{18}$ and $R_{19}$ are the same and are methyl or ethyl. For example, the siloxane precursor cross-linking compound may be tetraethylorthosilicate ($Si(OCH_2CH_3)_4$).

In order to react with the siloxane precursor cross-linking compound, a compound is provided that contains at least two hydrogen atoms attached to one or more nitrogen atoms.

It is to be noted that the "compound containing at least two hydrogen atoms attached to one or more nitrogen atoms" includes within its scope compounds in which one or more of the hydrogens are replaced by a protecting group so long as the compound contains at least one hydrogen attached to a nitrogen atom. In this case, after reaction with the cross-linking siloxane precursor group, the protecting group is de-protected exposing another hydrogen attached to a nitrogen atom. Alternatively, the hydrogen may be being protected by being replaced by a halogen (for example chlorine or bromine), in which case there is no need to de-protect the nitrogen because it already has some disease-preventing properties. In one embodiment, the compound does not contain a silicon atom.

In this aspect, the known disease-control properties of a N-halogen group is being taken advantage of. While certain compounds may be selected and certain processing conditions may be used to render a surface effective against toxins, the N-halogen group is known also to be effective against pathogens. Therefore, this aspect is not restricted to the specifically-selected groups of the first aspect of the invention but is much more widely applicable.

The "compound containing at least two hydrogen atoms attached to one or more nitrogen atoms" may be cyclic or acyclic. In one embodiment, it is cyclic. In one embodiment, the compound contains a functional group selected from the group consisting of hydantoin, imidazolidinone, glycoluril, isocyanurate, triazinedione and combinations thereof.

The hydantoin functional group in one embodiment has the following chemical formula:

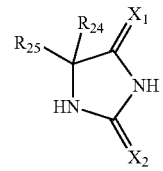

and derivatives thereof in which one of the NHs is either protected with a protecting group or is replaced by N-Halogen (in one embodiment N—Cl or N—Br). Protecting groups are well-known in the art (see, for example, the book "Protective Groups in Organic Synthesis" by Greene et al.).

In this formula, $X_1$ and $X_2$ are independently-selected optionally-substituted heteroatoms (i.e. atoms other than carbon). For example, $X_1$ and/or $X_2$ may be oxygen, nitrogen or sulphur. If either $X_1$ or $X_2$ is nitrogen, the nitrogen is substituted with a third substituent, i.e. $X_1$ and/or $X_2$ have the chemical formula $NR_7$. In a preferred embodiment, this third substituent ($R_7$) is hydrogen. Alternatively, $R_7$ (or any other optional substituent) may be OH, O-alkyl, O-heteroalkyl, alkyl or heteroalkyl.

In this formula, $R_{24}$ and $R_{25}$ are independently selected from hydrogen, the halogens (in one embodiment chlorine or bromine), alkyl, heteroalkyl and a siloxane monolayer precursor-containing group, OH, O-alkyl, O-heteroalkyl, $NH_2$, NH(alkyl), NH(heteroalkyl), N(alkyl)(alkyl), N(alkyl)(heteroalkyl) and N(heteroalkyl)(heteroalkyl).

The imidazlidinone functional group in one embodiment has the following chemical formula (it can have two forms):

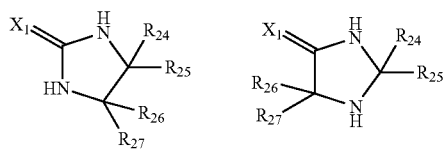

and derivatives thereof in which one of the NHs is either protected with a protecting group or is replaced by N-Halogen (in one embodiment N—Cl or N—Br). Protecting groups are well-known in the art (see, for example, the book "Protective Groups in Organic Synthesis" by Greene et al.).

In this formula, $X_1$ is an optionally-substituted heteroatom (i.e. an atom other than carbon). For example, $X_1$ may be oxygen, nitrogen or sulphur. If $X_1$ is nitrogen, the nitrogen is substituted with a third substituent, i.e. $X_1$ has the chemical formula $NR_7$. In a preferred embodiment, this third substituent ($R_7$) is hydrogen. Alternatively, $R_7$ (or any other optional substituent) may be OH, O-alkyl, O-heteroalkyl, alkyl or heteroalkyl.

In this formula, $R_{24}$, $R_{25}$, $R_{26}$ and $R_{17}$ are independently selected from hydrogen, the halogens (in one embodiment chlorine or bromine), alkyl, heteroalkyl and a siloxane monolayer precursor-containing group, OH, O-alkyl, O-heteroalkyl, $NH_2$, NH(alkyl), NH(heteroalkyl), N(alkyl)(alkyl), N(alkyl)(heteroalkyl) and N(heteroalkyl)(heteroalkyl).

The isocyanurate functional group in one embodiment has the following formula:

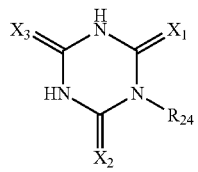

and derivatives thereof in which one of the NHs is either protected with a protecting group or is replaced by N-Halogen (in one embodiment N—Cl or N—Br). Protecting groups are well-known in the art (see, for example, the book "*Protective Groups in Organic Synthesis*" by Greene et al.).

In this formula, $X_1$, $X_2$ and $X_3$ are independently-selected optionally-substituted heteroatoms (i.e. atoms other than carbon). For example, $X_1$ and/or $X_2$ may be oxygen, nitrogen or sulphur. If either $X_1$ or $X_2$ is nitrogen, the nitrogen is substituted with a third substituent, i.e. $X_1$, $X_2$ and/or $X_3$ have the chemical formula $NR_7$. In a preferred embodiment, this third substituent ($R_7$) is hydrogen. Alternatively, $R_7$ (or any other optional substituent) may be OH, O-alkyl, O-heteroalkyl, alkyl or heteroalkyl.

In this formula, $R_{24}$ is selected from hydrogen, the halogens (in one embodiment chlorine or bromine), alkyl, heteroalkyl and a siloxane monolayer precursor-containing group, OH, O-alkyl, O-heteroalkyl, $NH_2$, NH(alkyl), NH(heteroalkyl), N(alkyl)(alkyl), N(alkyl)(heteroalkyl) and N(heteroalkyl)(heteroalkyl). $R_{24}$ may be a protective group for NH.

The triazinedione functional group in one embodiment has the following formula:

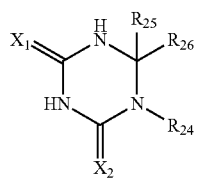

and derivatives thereof in which one of the NHs is either protected with a protecting group or is replaced by N-Halogen (in one embodiment N—Cl or N—Br). Protecting groups are well-known in the art (see, for example, the book "*Protective Groups in Organic Synthesis*" by Greene et al.).

In this formula, $X_1$ and $X_2$ are independently-selected optionally-substituted heteroatoms (i.e. atoms other than carbon). For example, $X_1$ and/or $X_2$ may be oxygen, nitrogen or sulphur. If either $X_1$ or $X_2$ is nitrogen, the nitrogen is substituted with a third substituent, i.e. $X_1$ and/or $X_2$ have the chemical formula $NR_7$. In a preferred embodiment, this third substituent ($R_7$) is hydrogen. Alternatively, $R_7$ (or any other optional substituent) may be OH, O-alkyl, O-heteroalkyl, alkyl or heteroalkyl.

In this formula, $R_{24}$, $R_{25}$ and $R_{26}$ are independently selected from hydrogen, the halogens (in one embodiment chlorine or bromine), alkyl, heteroalkyl and a siloxane monolayer precursor-containing group, OH, O-alkyl, O-heteroalkyl, $NH_2$, NH(alkyl), NH(heteroalkyl), N(alkyl)(alkyl), N(alkyl)(heteroalkyl) and N(heteroalkyl)(heteroalkyl). $R_{24}$ may be a protecting group for NH.

In one embodiment, the compound containing at least two hydrogen atoms is a glycoluril compound. In this case, the free NH is able to react with the siloxane precursor cross-linking compound. Alternatively, a group appending the glycoluril functional group may be capable of reacting with the siloxane precursor cross-linking compound. If one or more halogen atoms are not appended to any of the other atoms in the glycoluril functional group, then in one embodiment the glycoluril functional group contains at least two NH groups (the second one is then activated to become NCl).

In one embodiment, the glycoluril compound of this second aspect has the following chemical formula:

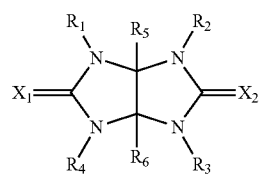

In this formula, $X_1$ and $X_2$ are independently-selected optionally-substituted heteroatoms (i.e. atoms other than carbon). For example, $X_1$ and/or $X_2$ may be oxygen, nitrogen or sulphur. If either $X_1$ or $X_2$ is nitrogen, the nitrogen is substituted with a third substituent, i.e. $X_1$ and/or $X_2$ have the chemical formula $NR_7$. In a preferred embodiment, this third substituent ($R_7$) is hydrogen. Alternatively, $R_7$ (or any other optional substituent) may be OH, O-alkyl, O-heteroalkyl, alkyl or heteroalkyl.

In this formula, $R_1$, $R_2$, $R_3$ and $R_4$ are independently selected from hydrogen, the halogens (in one embodiment chlorine or bromine), alkyl and heteroalkyl. $R_5$ and $R_6$ are independently selected from hydrogen, the halogens (in one embodiment chlorine or bromine), alkyl, heteroalkyl and a siloxane monolayer precursor-containing group, OH, O-alkyl, O-heteroalkyl, $NH_2$, NH(alkyl), NH(heteroalkyl), N(alkyl)(alkyl), N(alkyl)(heteroalkyl) and N(heteroalkyl)(heteroalkyl). At least one of $R_1$, $R_2$, $R_3$ and $R_4$ is hydrogen. If none of $R_1$, $R_2$, $R_3$ and $R_4$ are a halogen (in one embodiment chlorine or bromine) or a protecting group for NH, then in one embodiment at least two of $R_1$, $R_2$, $R_3$ and $R_4$ are hydrogen. Protecting groups are well-known in the art (see, for example, the book "*Protective Groups in Organic Synthesis*" by Greene et al.).

One advantage of using this method is that it is simpler and more convenient than the first aspect. Simply, all that has to be done is for the precursors to be mixed together rather than the synthesis of a specially-designed molecule incorporating both a glycoluril group and a siloxane monolayer precursor group. As such, this also represents an improvement on the methodology in U.S. Pat. No. 6,969,769, so this method can be used without the application of microwaves to form a conventional coating on a substrate (i.e. a coating that is not effective against toxins but can be used for other purposes).

Other preferred features of this second aspect are the same as those of the first aspect. For example, the surface coating, once formed, is treated in the same manner as in the first aspect to make N-halogen groups (for example N—Cl or N—Br groups).

In a third aspect, the present invention provides a substrate having a coating deposited according to the first or second aspect. As described in PCT/GB2006/03440, which is incorporated herein in its entirety by reference, depositing a coating using microwaves rather than heat results in a physical change in the properties of the coating. Therefore, a coating formed while being irradiated by microwaves is physically different from a coating formed simply by heating. Accordingly, the third aspect provides a substrate having compounds as defined in either the first or second aspects attached to, and/or organized into an array on the surface of the substrate.

In a fourth aspect, the present invention provides a novel glycoluril derivative that is especially adapted for use in the first and second aspects of the present invention. This glycoluril derivative has the chemical structure:

$$
\begin{array}{c}
R_1 \quad R_5 \quad R_2 \\
\diagdown N \diagup \diagdown N \diagup \\
HN = \diagdown \diagup = NH \\
\diagup N \diagdown \diagup N \diagdown \\
R_4 \quad R_6 \quad R_3
\end{array}
\quad (6)
$$

wherein:

$R_1$, $R_2$, $R_3$ and $R_4$, $R_5$ and $R_6$ are independently selected from hydrogen, the halogens (in one embodiment chlorine or bromine), alkyl, heteroalkyl, a group containing a siloxane monolayer precursor, OH, O-alkyl, O-heteroalkyl, $NH_2$, NH(alkyl), NH(heteroalkyl), N(alkyl)(alkyl), N(alkyl)(heteroalkyl) and N(heteroalkyl)(heteroalkyl), and at least one of $R_1$, $R_2$, $R_3$, $R_4$, $R_5$ and $R_6$ is a group containing a siloxane monolayer precursor.

This compound has been found by the inventor to be particularly effective when attached to a surface and used to deactivate toxins.

The preferred features of $R_1$ to $R_6$ are the same for this aspect as for the first and third aspects of the present invention.

In a fifth aspect, the inventor has found that the use of a siloxane monolayer precursor to attach a glycoluril functional group to a surface has certain disadvantages. Therefore, the inventor has sought new ways of forming disease-preventing coatings containing a glycoluril functional group on a surface. Accordingly, in a fifth aspect, the invention provides certain precursors for forming a coating containing a glycoluril functional group that is effective against toxins. These precursors have the following chemical structure:

$$
\begin{array}{c}
R_1 \quad R_5 \quad R_2 \\
\diagdown N \diagup \diagdown N \diagup \\
X_1 = \diagdown \diagup = X_2 \\
\diagup N \diagdown \diagup N \diagdown \\
R_4 \quad R_6 \quad R_3
\end{array}
\quad (7)
$$

$R_1$ to $R_6$ are as defined previously. At least one or $R_1$ to $R_6$ is a group containing a vinyl group, an imide, an acrylate, an alkene, an epoxide or an alkyl halide.

These precursors are more convenient to prepare than their siloxane monolayer precursor equivalents.

In a sixth aspect, the present invention provides a method for forming a coating on a substrate by applying the compound (7) to a surface and allowing it to form a coating on the surface. The coating may be formed or cured by heat or microwaves.

In a seventh aspect, the present invention provides a substrate coated with a coating formed by the sixth aspect of the present invention.

The present invention also provides the use of the coatings described above in the deactivation of toxins. These coatings may be formed from, for example, a compound containing a glycoluril functional group and a siloxane monolayer precursor group or compound (7).

In one test process the synthesis of glycoluril crosslinked aluminium oxide may be achieved where Boehmite aluminium oxide is wetted with a basic water-alcohol solution containing glycoluril and tetraethylorthosilicate. The boehmite may then be irradiated with microwaves for three one minute intervals, washed thoroughly, and allowed to dry.

The product may be chlorinated via 30 minute wash in 0.5% aqueous sodium hypochlorite, washed thoroughly, and dried overnight at room temperature under vacuum. The presence of oxidative chlorine may be confirmed via colorimetric reaction with potassium iodide and starch indicator solution.

The synthesis of hydantoinylated aluminium oxide may be confirmed by wetting boehmite aluminium oxide with a basic water-alcohol solution containing 1-hydroxymethyl-5,5-dimethyl hydantoin and tetraethylorthosilicate. The boehmite may then be irradiated with microwaves for three one minute intervals, washed thoroughly, and allowed to dry. The product from this may be titrated via iodometry. Test results may be found to contain 8 ppm of active, oxidative chlorine. From previous experiments it is believed that >2 ppm of active chlorine is sufficient to inactivate toxins via denaturation.

The ability of the chlorinated glycoluril crosslinked boehmite to deactivate toxins may be confirmed via standard enzyme inhibition studies using three representative toxin simulants, nitrobenzene nitroreductase, lysozyme, and laccase. In each case the chlorinated glycoluril boehmite may have more than 99.9% reduction in enzyme activity as compared to control cases. The control cases may be untreated boehmite, treated unchlorinated glycoluril boehmite, and the representative enzyme solution without a solid matrix.

Although preferred features described above have been described in relation to certain embodiments, it will be readily apparent to the person skilled in the art that preferred features of one embodiment are readily applicable to the other embodiments.

What is claimed is:

1. A compound having a structure:

$$
\begin{array}{c}
R_1 \quad R_5 \quad R_2 \\
\diagdown N \diagup \diagdown N \diagup \\
HN = \diagdown \diagup = NH \\
\diagup N \diagdown \diagup N \diagdown \\
R_4 \quad R_6 \quad R_3
\end{array}
$$

wherein:

$R_1$, $R_2$, $R_3$ and $R_4$, $R_5$ and $R_6$ are independently selected from hydrogen, the halogens, alkyl, heteroalkyl, a group containing a siloxane monolayer precursor, OH, O-alkyl, O-heteroalkyl, NH2, NH(alkyl), NH(heteroalkyl), N(alkyl)(alkyl), N(alkyl)(heteroalkyl) and N(heteroalkyl)(heteroalkyl), and at least one of $R_1$, $R_2$, $R_3$, $R_4$, $R_5$ and $R_6$ is a group containing a siloxane monolayer precursor.

2. A method for forming a coating for deactivation of toxins on a substrate, comprising the steps of:

providing a compound having a structure:

$$\begin{array}{c}\text{R}_1\phantom{xxx}\text{R}_5\phantom{xxx}\text{R}_2\\ \diagdown\phantom{x}\text{N}\phantom{xx}|\phantom{xx}\text{N}\phantom{x}\diagup\\ \text{X}_1=\phantom{xxxxxxxxxx}=\text{X}_2\\ \diagup\phantom{x}\text{N}\phantom{xx}|\phantom{xx}\text{N}\phantom{x}\diagdown\\ \text{R}_4\phantom{xxx}\text{R}_6\phantom{xxx}\text{R}_3\end{array}$$

wherein:

$X_1$ and $X_2$, are independently-selected heteroatoms, optionally having one or more pendant independently-selected alkyl and/or independently-selected heteroalkyl groups and/or hydrogen, $R_1$, $R_2$, $R_3$ and $R_4$, $R_5$ and $R_6$ are independently selected from hydrogen, the halogens, heteroalkyl, OH, O-alkyl, O-heteroalkyl, NH2, NH(alkyl), NH(heteroalkyl), N(alkyl)(alkyl), N(alkyl)(heteroalkyl) and N(heteroalkyl)(heteroalkyl), and at least one of $R_1$, $R_2$, $R_3$, $R_4$, $R_5$ and $R_6$ is a group containing a vinyl group, an imide, an acrylate, an alkene, an epoxide or an alkyl halide, applying the compound to the surface, and exposing the surface to microwave electromagnetic radiation.

3. A substrate having a compound attached to, and/or organized into an array on the substrate by being treated by the method as defined in claim 2.

\* \* \* \* \*